United States Patent [19]

Carver, Jr.

[11] Patent Number: 5,486,477
[45] Date of Patent: Jan. 23, 1996

[54] REAGENT SYSTEM FOR IMPROVED MULTIPLE SPECIES BLOOD ANALYSIS

[76] Inventor: Edward L. Carver, Jr., 18 Lisa Dr., Oxford, Conn. 06483

[21] Appl. No.: 105,027

[22] Filed: Aug. 11, 1993

Related U.S. Application Data

[62] Division of Ser. No. 57,212, May 3, 1993, Pat. No. 5,262,329, which is a continuation of Ser. No. 714,671, Jun. 13, 1991, abandoned.

[51] Int. Cl.⁶ .................................................. G01N 1/28
[52] U.S. Cl. ................................ 436/17; 436/18; 422/61
[58] Field of Search ................................ 436/8, 10, 15, 436/17, 18, 63, 176; 422/61

[56] References Cited

U.S. PATENT DOCUMENTS

| | | | |
|---|---|---|---|
| 3,634,581 | 1/1972 | Thomas | 424/3 |
| 3,741,875 | 6/1973 | Ansley et al. | 195/103.5 |
| 4,213,876 | 7/1980 | Crews et al. | 252/408 |
| 4,286,963 | 9/1981 | Ledis et al. | 23/230 |
| 4,346,018 | 8/1982 | Carter et al. | 252/408 |
| 4,485,175 | 11/1984 | Ledis et al. | 436/63 |
| 4,529,705 | 7/1985 | Larsen | 436/17 |
| 4,745,071 | 5/1988 | Lapicola et al. | 436/63 |
| 4,751,179 | 6/1988 | Ledis et al. | 435/34 |
| 4,962,038 | 10/1990 | Carter et al. | 436/10 |
| 5,155,044 | 10/1992 | Ledis et al. | 436/17 |
| 5,180,677 | 1/1993 | Di Ianni et al. | 436/17 |

FOREIGN PATENT DOCUMENTS

| | | |
|---|---|---|
| 0424871 | 5/1991 | European Pat. Off. . |
| 0444241 | 9/1991 | European Pat. Off. . |
| 53-100298 | 1/1978 | Japan . |
| 8807187 | 9/1988 | WIPO . |

*Primary Examiner*—Jeffrey R. Snay
*Attorney, Agent, or Firm*—Cummings & Lockwood

[57] ABSTRACT

The present invention provides a novel lytic reagent composition highly selective in its interactions with the cell membranes of blood cells and also provides a method of using the reagent composition in a semi-automated or an automated system to effect a significantly improved white blood cell differential determination. The lytic reagent composition is characterized by an ability to selectively shrink the white blood cells into the increasing size order of lymphocytes, a midregion consisting mainly of monocytes, other mononuclear cells, some basophils and eosinophils, and neutrophils and can readily be optimized to effect a significantly improved three component separation on the histogram of commercially available semi-automated and automated blood analyzers when compared to the reagents conventionally employed on such instruments. Also provided is a novel blood diluent that exhibits an improved ability to stabilize blood cells without "fixing" the permeability of their membranes, which is critical in the semi-automated analysis of blood cells. This mechanism for membrane stability is particularly effective for maintaining the morphology and size distribution of blood cells for multiple species of animals.

12 Claims, 6 Drawing Sheets

5,486,477

REAGENT SYSTEM FOR IMPROVED MULTIPLE SPECIES BLOOD ANALYSIS

This is a division of application Ser. No. 08/057,212 filed May 3, 1993, now U.S. Pat. No. 5,262,329, which is a continuation of application Ser. No. 714,671 field Jun. 13, 1991, now abandoned.

FIELD OF THE INVENTION:

This invention relates to an improved reagent system for blood analysis including a lytic reagent composition for the differentiation of more than one class of leukocyte subpopulations. When combined with the blood diluent of the present invention, the lyric reagent composition of the invention is characterized by an ability to consistently effect a very clean separation of white blood cells into three or more subpopulations on a leukocyte volume histogram, with little or no cellular debris. The lytic reagent composition can, in practice, enable the classification and counting of several subpopulations of white blood cells. Such data are extremely useful for the detection of abnormal distributions in subpopulations of mature white blood cells and morphological abnormalities in a blood sample.

The blood diluent of the present invention utilizes a dilute concentration of a monoaldehyde for both stabilizing the membranes of blood cells and serving as an antimicrobial agent. This mechanism for membrane stability is effective for maintaining the morphology and size distribution of blood cells for multispecies of animals without requiring the inclusion of numerous additives.

The instant invention is an extremely efficient reagent system for both semi-automated and automated instrumentation, but is particularly suited for semi-automated analyses.

BACKGROUND OF THE INVENTION

It is a common medical diagnostic procedure to test a blood sample in order to determine the health state of the patient. The hematology panel of tests routinely includes the analysis of red blood cells, their associated morphological indices such as mean corpuscular volume and red blood cell distribution width, hemoglobin, platelets, mean platelet volume and white blood cell differentiation. This panel of tests has previously only been performed on large, expensive and complex instrumentation, but there has been a growing need for less expensive instrumentation that delivers precise and accurate data for all hematology measurements.

In addition, further demands have been placed on instrumentation to analyze more than one species of animals. This need stems from numerous tests that are performed in order to prove the clinical utility of pharmaceutical products, routine analysis of livestock, and the desire to take better care of pets. It has been difficult to generate useful clinical data for multiple animal species from one instrument. This has been a complex problem because the quantity, size, and blood cell membrane permeability has a great deal of variability from one species of animal to the next.

In blood analysis, particular clinical utility has been given to the white blood cells. Within the white blood cell population, many subpopulations exist, five of which are considered predominantly in hematological analysis. These white cell subpopulations include polymorphonuclear neutrophils, which constitute from about 45–80% of the mature white blood cells in a population; monomorphonuclear lymphocytes, which constitute about 15–45% of the white blood cells in a normal mature population; monomorphonuclear monocytes (~0–5%); polymorphonuclear eosinophils (~0–5%); and polymorphonuclear basophils (0–3%). In many diseases, there is a clinically significant alteration in the normal distribution of these mature cell types. In addition, immature or abnormal cell types are often associated with the disease state. Hematological analysis of white blood cells, including white cell enumeration and flagging of abnormalities, in conjunction with traditional diagnostic techniques, is thus an important tool in the diagnosis and treatment of disease.

Prior to the mid-1970's, white blood cell differential analyses were conducted by manual examination, with a technician viewing blood film slides with the aid of a microscope. Since that time, hematological analysis has been automated, making its use both widespread and commonplace.

While the methodologies for automated analysis vary, most often the enumeration and analysis involves subjecting a diluted sample of whole blood to a lysing reagent which stromatolyzes and therefore eliminates the red blood cell population and simultaneously modifies the cell membranes of the more prevalent white cell subpopulations so that the cytoplasm leeches out, causing differential shrinkage of the different cell types and enabling discrimination and sorting thereof. The size and number of white blood cells in the sample are then detected with the aid of a semi-automated or an automated analyzer, which typically includes a detector adapted to detect the volume (size) or opacity of the white blood cells in the sample by electrical or optical differences. The white blood cells are counted for a period of time sufficient to gather data for analysis, data points are stored in a memory device and then analyzed in an algorithmic processor. The data can then be displayed in the form of a two dimensional or three dimensional histogram.

Heretofore, a number of lysing reagents and reagent systems have been developed which have provided the clinician with the ability to isolate the white cell population from the red cell population of whole blood and to further differentiate the white cell population into smaller subpopulations. Patents considered representative of the art in the field include U.S. Pat. Nos. 3,741,875; 4,286,963; 4,346,018; 4,485,175; 4,529,705; 4,745,071; 4,751,179 and WO88/07187.

U.S. Pat. No. 3,741,875 to Ansley et al describes the use of a cytological fixing agent to kill the blood cells in a fluid sample in order to immobilize the catalytic enzymes contained within the cells. The cytological fixing agent is a concentrated monoaldehyde that must be strong enough (up to 40%) to kill the cells without destroying the activity of enzymes. The methodology of Ansley involves the addition of a specific cytochemical substitute, chromogenic precipitating coupling reagent, and pH buffer after the blood cells have been killed by the monoaldehyde, which causes deposition of an insoluble dye in a specific type of cell containing the immobilized enzyme. The solution containing the dyed blood cells is passed through a photometric counter which gives a count of the dyed cells.

U.S. Pat. No. 4,286,963 to Ledis et al describes a lytic diluent and method for achieving rapid lysis of red blood cells in whole blood. This diluent enhances the ability of automated instrumentation to perform differential determinations of lymphoid and myeloid subpopulations of leukocytes and the quantitative determination of hemoglobin. The lytic diluent employed by Ledis et al is composed of a mixture of at least one quaternary ammonium salt and an aryl substituted short chain alkanol in buffered aqueous medium (pH 3.5 to 5.0). The lytic diluent of this Ledis et al patent is limited in its ability to effect differentiation of the leukocyte population into the two principal subpopulations; namely the lymphoid and myeloid fractions.

U.S. Pat. No. 4,346,018 to Carter et al describes an isotonic blood diluent comprising numerous additives that act as a cell stabilizing mixture of organic buffers, anesthetics, and germicides. Of these ingredients, N-(2-acetamido) iminodiacetic acid (ADA) is a necessary ingredient for stabilizing the size distribution and cellular shape of platelets and erythrocytes. Dimethylolurea is required as a neutral pH in order to afford a measure of stability to the leukocyte membranes.

U.S. Pat. No. 4,485,175, also to Ledis et al, describes a reagent system and method for performance of differential determinations of leukocytes into three subpopulations utilizing automated cell counting equipment, in which the reagent system includes a blood diluent and lysing reagent. The lysing reagent comprises an aqueous mixture of aliphatic quaternary ammonium compounds, which when added to a diluted blood sample under mild conditions of concentration and at a relatively slow rate causes volume modifications to the various subpopulations of white blood cells, enabling a three component separation.

U.S. Pat. No. 4,529,705 to Larsen relates to a reagent for combined diluting and lysing of whole blood cells. The reagent comprises an aliphatic quaternary ammonium salt and at least one anion selected from the group consisting of sulfate, carbonate, formate and acetate anions, which are employed for the purpose of preventing aggregation of platelets in the sample and an alkali metal cyanide for conversion of hemoglobin to a chromagen.

U.S. Pat. No. 4,745,071 to Lapicola describes a reagent system for differential blood analysis including a blood diluent and lysing reagent. The lysing reagent of the '071 patent comprises an aqueous solution of a single aliphatic quaternary ammonium salt and may also contain potassium cyanide as a chromagen forming agent. The preferred quaternary ammonium salt is the dodecyl ($C_{12}$) homolog.

U.S. Pat. No. 4,751,179 to Ledis et al describes a reagent system, using saponin as a lysing reagent followed by treatment with a rapidly active cross linking agent such as glutaraldehyde as a fixing reagent. The dialdehyde, preferably glutaraldehyde, must be present in sufficient concentration (0.5–4.0%) to stop the lyric activity of the saponin, and slow acting monoaldehydes, such as formaldehyde, have been determined to be ineffective for preserving the leukocytes in this reaction.

WO88/07187 describes a reagent system enabling differentiation of white blood cells into at least five distinct subpopulations. The PCT application discloses a reagent system comprising a lyric reagent and a companion reagent for the lyric reagent referred to as a "quench". The primary functions of the quench are to retard the activity of the lytic reagent and to restore the ionic balance of the sample subsequent to its treatment with lyric reagent.

Generally, the white blood cell differentials obtained in accordance with the described techniques fall into one of two categories. The first category is a three component screening differential resulting in the isolation and quantification of three fractions of white blood cells including a lymphocyte component, a midregion or monocyte component and a granulocyte (predominantly neutrophilic) component. The granulocyte population usually includes the neutrophils, as well as eosinophils, and possibly basophils, while the midregion often contains monocytes, other mononuclear cells, basophils and eosinophils. Separation among populations is frequently poor, resulting in low correlation between automated and manual differential counts, which is undesirable. Poor separation of subpopulations is further undesirable as it decreases the ability to accurately flag abnormalities.

The second category of white blood cell analyzers is capable of effecting a four or five component separation. Such systems are substantially more complex than the three component differential analyzers, resulting in higher costs to the operator for materials and labor. An illustration of this type of system is described in WO88/07187, a Patent Cooperation Treaty application to Coulter Electronics.

After extensive investigation, it has been determined that the gentle lytic activity achieved by using a single quaternary ammonium salt consisting of either dodecyltrimethyl ammonium salt or dodecyldimethyl ethylammonium salt will indeed preserve infrequent and rare leukocytes, but the identification of abnormalities is hindered because these detergents are non-specific and non-selective to various leukocyte membranes. This non-specificity causes poor definition of these subpopulations, and results in a high degree of overlap, poor correlation to standard methods, and an inability to consistently flag abnormalities.

It has also been determined that the use of a mixture of quaternary ammonium salts as described in previous patents will result in too harsh of lytic activity to provide proper differentiation of subpopulations for semi-automated instruments.

Accordingly, it is an object of the present invention to provide an improved lytic reagent composition which selectively modifies blood cell volume by reacting with the cell membranes to cause red blood cells to rupture and selectively shrinks the white blood cell population into at least three distinct, highly separated components when used in combination with a suitable blood diluent.

Another object of the present invention is to provide a blood diluent capable of providing a stabilized environment to effectively analyze the size distribution of red blood cells, platelets and white blood cells on semi-automated instruments.

A still further object of the present invention is to provide a flexible reagent system for multispecies blood analysis.

A still further object of the present invention is to provide a blood diluent that does not require pH or osmolality optimization for each species in order to be species specific, or a neutral pH to effect a proper leukocyte differential.

Yet another object of the invention is to provide an improved method for semi-automated white blood cell differential analysis.

Further objects and advantages will be appreciated from the following disclosure.

SUMMARY OF THE INVENTION

These as well as related objects are achieved in accordance with the present invention, which provides a novel lytic reagent composition highly selective in its interactions with the cell membranes of blood cells and also provides a method of using the reagent composition in a semi-automated or an automated system to effect a significantly improved white blood cell differential determination. The lytic reagent composition is characterized by an ability to selectively shrink the white blood cells into the increasing size order of lymphocytes, a midregion consisting mainly of monocytes, other mononuclear cells, some basophils and eosinophils, and neutrophils and can readily be optimized to effect a significantly improved three component separation on the histogram of commercially available semi-automated and automated blood analyzers when compared to the reagents conventionally employed on such instruments.

The lytic reagent composition of the instant invention comprises an aqueous solution of active lytic reagents consisting essentially of at least one heterocyclic quaternary ammonium compound, wherein the quaternary compound can be represented by the formula:

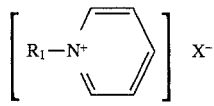

wherein $R_1$ is a long chain alkyl radical comprising from 8 to 20 carbon atoms and X is an ion selected from the group consisting of a halide, sulfate, phosphate, and nitrate.

The use of an aqueous solution of at least one of these quaternary compounds results in a lytic reagent composition that will selectively modify the cell membrane of white blood cells and is capable of effecting at least a three component separation of white blood cells into lymphocytes, a midregion consisting predominantly of monocytes, other mononuclear cells, some basophils and eosinophils, and neutrophil subpopulations on a leukocyte volumetric histogram.

Also provided is a novel blood diluent that exhibits an improved ability to stabilize blood cells without "fixing" the permeability of their membranes, which is critical in the semi-automated analysis of blood cells. More specifically, with respect to the diluent, it has been determined that the inclusion of a monoaldehyde, preferably formaldehyde, in a blood diluent in a dilute concentration in the range of 0.01% to 0.15%, provides superior cell stability and anti-microbial action. Stabilization of blood cell membranes with a blood diluent including formaldehyde permits the use of a variety of organic buffers without the necessity of numerous other additives, which can be costly and possibly interfere with the blood analysis. In addition, the blood diluent has proven to provide effective cell stability for a variety of animal species without the need to adjust the diluent pH and osmolality for each species.

These effects are most prevalent when a blood sample is analyzed on a semi-automated instrument where the sample is externally prediluted with the diluent prior to counting. In this situation, the erythrocyte/platelet dilution must maintain stable cell volumes and a high degree of cellular dispersion for various lengths of time because of operator variability. The diluent must also be capable of maintaining the white blood cell dilution for various lengths of time without "fixing" the red or white cell membranes. If the white cell membranes become fixed, the separation of the leukocyte subpopulations becomes difficult and if the red blood cell membranes become fixed, the red blood cells will not lyse, causing excessive cellular debris.

White blood cell differentiation on a semi-automated or an automated particle analyzer in accordance with the present invention is made possible by the use of the novel lytic reagent composition of the present invention in combination with a suitable blood diluent. The blood diluent preferably comprises at least one organic buffer and a monoaldehyde as an antimicrobial and cell membrane stabilizing reagent. The method of the invention comprises (1) supplying a whole blood sample, a volume of blood diluent and a volume of the lytic reagent composition to an automated or semi-automated particle analyzing system; (2) rapidly admixing the whole blood sample, the blood diluent and the lytic reagent composition of the present invention, wherein the heterocyclic quaternary compound components in the lytic reagent composition are present in a total concentration sufficient to effect at least a three component separation of white blood cells; and (3) analyzing the whole blood sample in the automated or semi-automated particle analyzer to differentiate and quantify at least one of the white blood cell subpopulations.

Red blood cell and platelet analysis on a semi-automated or an automated particle analyzer in accordance with the present invention is made possible by the use of the novel blood diluent. The red blood cell and platelet analysis is effected (1) supplying a whole blood sample and a volume of blood diluent to a chamber on the automated or semi-automated analyzer; (2) thoroughly admixing the whole blood sample, and the blood diluent; (3) analyzing the whole blood sample in the automated or semi-automated particle analyzer to differentiate and enumerate the red blood cell and platelet populations.

BRIEF DESCRIPTION OF THE DRAWINGS

FIG. 8 shows a three component separation of white blood cells on an increasing size order with cellular debris to the far left and neutrophils to the far right.

DETAILED DESCRIPTION OF THE INVENTION

Figure 1:
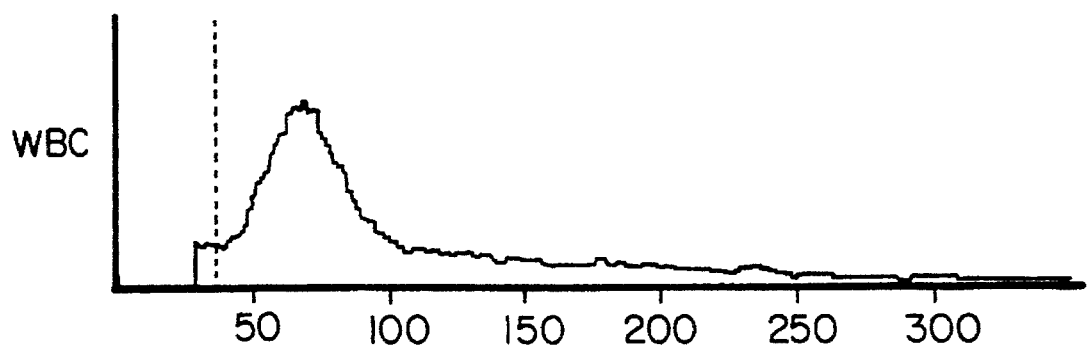
FIG. 1 is a leukocyte volume histogram showing the distribution of a patient with lymphocytosis, obtained using the lyric reagent and blood diluent of the present invention.

The reagent system of the present invention includes a novel blood diluent, wherein a monoaldehyde is included as the cell stabilizing means and antimicrobial reagent. This blood diluent is effective for the analysis of red blood cells, platelets, and white blood cells, for multiple species of animals. The reagent system of the present invention also comprises a novel lytic reagent composition which, when combined with the diluent of the present invention and a sample of whole blood, is capable of effectively removing the red blood cell population and consistently effecting a significantly improved separation of white blood cells on a volumetric histogram of a semi-automated or an automated blood analyzer.

The Lytic Reagent

After an extensive investigation, the inventors herein have discovered that long chain alkyl heterocyclic compounds, either alone or in combination, are highly specific for white blood cell membranes and can be used to improve the separation of white blood cell subpopulations on a volumetric histogram. The lytic reagent composition of the present invention comprises an aqueous solution of active lytic reagents consisting essentially of at least one heterocyclic quaternary compound that can be represented by the general formula:

wherein $R_1$ is a long chain alkyl radical comprising from 8 to 20, and preferably 12 carbon atoms and X is an ion selected from the group consisting of halide, phosphate, nitrate and sulfate ions. Preferred quaternary ammonium compound in accordance with the present invention include the 1-dodecyl pyridinium halides and hexadecyl pyridinium halides, with 1-dodecyl pyridinium chloride being particularly preferred.

The lytic reagent composition of the present invention is prepared by admixing the heterocyclic quaternary ammonium compound(s) in water, which preferably has been deionized. The mixture of the ingredients is done mechanically by moderate stirring over a suitable period of time.

The optimum quantity of the individual components of the active lytic reagents may vary, depending upon, for example, the chemical activity of the compounds selected and the individual instrument to be utilized in the differential analysis. Optimization of the quantity within the ranges provided is considered well within the skill in the art and can be achieved, for example, by varying the amount of the quaternary ammonium compound component in the lytic reagent composition, conducting an analysis on the particular analyzer to be used and conducting an ocular trauma test to determine the quantity which effects the cleanest separation on the leukocyte histogram.

The total concentration of the heterocyclic quaternary ammonium compound in the lytic reagent composition will typically be from about 7 to about 370 gms/liter. It should be understood, however, that the concentration of the active lytic species in the composition can be altered if the volume of the lytic reagent composition is modified accordingly.

To form a suitable chromagen for hemoglobin determination, as is desired for operation of most of the commercially available automated blood analyzers, the lytic reagent composition of the present invention can also be provided with an alkali metal cyanide, such as potassium cyanide (KCN). Other chromagen agents can also be employed. It should be appreciated, however, that the alkali metal cyanide is an optional ingredient used to accomplish a hemoglobin determination and is not critical for achieving a multi-component separation of white blood cells on a volumetric histogram in accordance with the present invention.

A particularly preferred formulation for the lytic reagent composition is:

| Ingredient | Preferred Formulation |
| --- | --- |
| 1-dodecyl pyridinium chloride | 69 gm/liter |
| KCN | 0.75 gm/liter |
| water | sufficient for 1 liter |

The Blood Diluent

In addition to diluting the blood sample for enumeration, the purpose of the diluent system in blood analysis is to suitably stabilize cell size, shape and integrity of all of the blood cellular components both before and after treatment with the lytic reagent composition, in order to promote the diagnostic accuracy of blood histograms derived from semi-automated and automated hematology analyzers. For these purposes, the blood diluent of the present invention requires the inclusion of a monoaldehyde. The monoaldehyde, which preferably is formaldehyde, is used in a concentration range of 0.01 to 0.15% and serves in this concentration as both an antimicrobial agent and as a means for achieving blood cell stabilization. When the monoaldehyde is included in the blood diluent, no additional reagents are required to aid in this purpose. In fact, it has been determined that the numerous additives conventionally used to preserve cellular morphology and stability may interfere with leukocyte membrane permeability causing too rapid of a lytic action, or insufficient lytic action, which may necessitate special mixing requirements or gradual addition of lyse.

A preferred formulation of the isotonic diluent of the present invention is:

| Ingredient | Effective Conc. Range | Most Preferred |
| --- | --- | --- |
| sodium sulfate | 7.5–12.5 gm/liter | 9.7 gm/liter |
| sodium chloride | 3.0–5.0 gm/liter | 4.0 gm/liter |
| organic buffer | 0.1–4.0 gm/liter | 2.0 gm/liter |
| formaldehyde | 0.1–1.5 ml/liter | 1.0 ml/liter |
| water | sufficient for one liter | |

A suitable acid or base, such as hydrochloric acid (HCl) or sodium hydroxide (NaOH), respectively, is used to adjust pH to desired level of pH 7.1±1.4, while sodium chloride (NaCl) is used to adjust osmolality to desired level of 325±50 mOs/kg.

The organic buffers which can be used in the blood diluent include ADA (N-[2-Acetamido]-2-iminodiacetic acid; N-carbamoylmethyl] iminodiacetic acid), MOPS (3-[N-Morpholino]propanesulfonic acid), PIPES (Piperazine-N, N'-bis[2-ethanesulfonic acid]; 1,4-Piperazinediethanesulfonic acid), HEPES (N-[2-Hydroxyethyl]piperazine-N'-[2-ethanesulfonic acid), BES (N,N-bis[2-Hydroxyethyl]-2-aminoethanesulfonic acid; 2-[bis(2-Hydroxyethyl)amino] ethanesulfonic acid), BIS-TRIS (bis[2-Hydroxymethyl]-methane; 2-bis[2-Hydroxyethyl]-amino-2-[hydroxymethyl] -1,3-propanediol), TES (N-tris[Hydroxymethyl]-2-aminoethanesulfonic acid; 2-([2-Hydroxy-1,1-bis(hydroxymethyl)-ethyl]amino)ethanesulfonic acid), TAPSO (3-[N-tris(Hydroxymethyl) methylamino]-2-hydroxy-propanesulfonic acid), MES (2-[N-Morpholino] ethanesulfonic acid), DIPSO (3-[N,N-bis(2-Hydroxyethyl)amino]-2-hydroxypropanesulfonic acid), MOPSO (3-[N-Morpholino]-2-hydroxypropanesulfonic acid), TRIS (tris [hydroxymethyl]aminomethane), ACES (2-[2-Amino-2-oxoethyl)amino]ethanesulfonic acid; N-[2-Acetamido]-2-aminoethanesulfonic acid). BES and ADA are particularly preferred.

The described diluent will produce accurate histograms with virtually any of the automated or semi-automated blood analyzers but will produce significantly improved three component histograms when used in conjunction with the lytic reagent composition of the present invention on a semi-automated particle analyzer.

The Method

In accordance with the inventive methodology, a whole blood sample, a volume of the blood diluent and a volume of the lytic reagent composition are supplied to a semi-automated or an automated analyzer and rapidly admixed therein, such that the heterocyclic quaternary ammonium compound components in the lytic reagent composition are present in a total concentration sufficient to effect at least a three component separation of white blood cells and then using the semi-automated or automated analyzer to differentiate and quantify at least one of the white blood cell subpopulations.

According to the known operation for the Unipath CELL-DYN® 1500 Semi-automated hematology analyzer, which can utilize the present invention, a mixture of whole blood is prediluted by an external diluter. The separate WBC/Hb and RCB/PLT dilutions are then placed onto the cell analyzer where the lytic agent of the present invention is then rapidly added and mixed for the WBC/Hb analysis. In accordance with the present invention, by using a combination of a diluent containing a monoaldehyde, preferably formaldehyde, and a lytic reagent containing a heterocyclic quaternary ammonium compound, preferably 1-dodecyl pyridinium chloride, the lytic reagent composition provides a combination that is highly selective for the membranes of various white blood cell subpopulations and is capable of effecting a volumetric separation of the white blood cells into at least three visible subpopulations.

In a preferred embodiment for the WBC differential dilution, the lytic reagent composition is first admixed with an initial volume of diluent. The whole blood sample is then dispensed into the thus prepared lyse/diluent mixture, with a second volume of diluent. In accordance with this embodiment, the initial volume of diluent can be varied in order to adjust the lytic strength of the reagent composition, while the final volume of diluent can be varied in order to adjust the final dilution ratio.

The final ratio of blood diluent to lytic reagent composition for white blood cell analysis will typically be from about 5:1 to about 250:1 and the final dilution of the blood will be from about 5 to 1000, generally about 250 parts by volume total diluent and lytic reagent composition per part by volume of the whole blood sample. The quantity of total active lytic reagents to the volume of blood in the counting cuvette of the analyzer should range from about 0.15 mg total active lytic reagents/μl whole blood to about 3.2 mg total active lytic reagents/μl whole blood.

In a preferred embodiment for the red blood cell/platelet dilution, a portion of the diluent is dispensed into the mixing chamber. The whole blood sample is then dispensed into the mixing chamber with a second volume of diluent at a sufficient rate to ensure thorough mixing. Care must be taken to not create microbubbles that could be counted as platelets.

The final dilution of the blood sample to diluent will typically be from about 500 to 50,000, generally about 12,500 parts by volume total diluent per part by volume of the whole blood sample.

It should be appreciated that the above values are only examples based upon successful formulations and reasonable deviations therefrom also will provide useful results in achieving the objects of the invention.

In the automated analyzer, the whole blood/reagent system mixture remains in the lysing chamber for a short but sufficient amount of time for the red blood cells to be stromatolyzed and release their hemoglobin and for the active lytic reagents to act on the cell membranes of the white blood cells and cause them to shrink. As will be readily appreciated by persons skilled in this area of technology, the incubation times may vary depending on factors such as the strength of the active lytic reagents used in the lytic reagent composition and the total final concentration of the active lytic reagent in the sample. As a general guideline, for human blood analysis, the whole blood/reagent system mixture will generally remain in the lysing chamber for a period of time ranging from about 10 to about 30 seconds. The determination of the precise incubation time for a given reagent system in accordance with the present invention can be readily accomplished by persons skilled in the art.

The suspension resulting from the foregoing is then passed through sensing aperture(s) in a leukocyte counting bath, wherein the white blood cells are counted and the volume (size) and/or opacity is measured by electrical or optical differences. There, the white blood cells are counted for a period of time to gather sufficient data for analysis, typically about 10,000 cells. The data points are stored and analyzed in a histogrammer, and visually displayed on a white blood cell histogram such as the one illustrated in FIG. 2.

When utilized on commercially available differential analyzers, the lytic reagent compositions of the present invention are capable of showing an improved three component separation of white blood cells when compared to the reagent systems typically employed on such analyzers. This aspect of the invention is illustrated in Example 2 herein, wherein exemplary lytic reagent composition within the scope of the present invention was comparatively tested on the CELL-DYN® 1500 semi-automated analyzer.

In order to optimize for an improved three component separation on other manufacturers' instruments, it is necessary to determine the optimum total concentration of active lytic reagents in the lysing composition. Since most commercial analyzers are fixed in terms of diluent volumes, blood volume, end point dilution ratios, and incubation time, the only variables to be optimized for any given instrument are the total quantity of the active lytic reagents.

EXAMPLE 1

This example illustrates the preparation of a preferred lytic reagent composition of the present invention and the use of the lytic reagent composition in a semi-automated differential analyzer to effect a three component separation of white blood cells from a sample of human whole blood.

An example of a preferred lytic reagent composition in accordance with the invention was formulated in accordance with the following:

| Component | Amount per liter |
|---|---|
| 1-dodecyl pyridinium chloride | 69.0 gm/liter |
| KCN | 0.75 gm/liter |
| water | sufficient to make one liter |

This lytic reagent composition is suitable for use with diluted blood samples. In this example, the blood diluent was the novel diluent of the present invention having the following formulation:

| Component | Amount per liter |
|---|---|
| sodium sulfate | 9.7 gm/liter |
| sodium chloride | 4.0 gm/liter |
| organic buffer | 2.0 gm/liter |
| formaldehyde | 1.0 ml/liter |
| water | sufficient for one liter |

A 40 μl sample of whole blood was dispensed into the counting cuvette of the semi-automated analyzer with 9.0 ml. of the blood diluent. The counting cuvette was placed on the semi-automated instrument. 1 ml. of the lytic reagent composition was dispensed into the counting cuvette for a total volume of 10 ml. and then thoroughly mixed.

The diluted sample was analyzed for leukocyte volume and enumeration by electronic resistance measurements of the sample passing through an orifice. Scanning was conducted for 10 seconds after addition of the reagent system.

Figure 2:
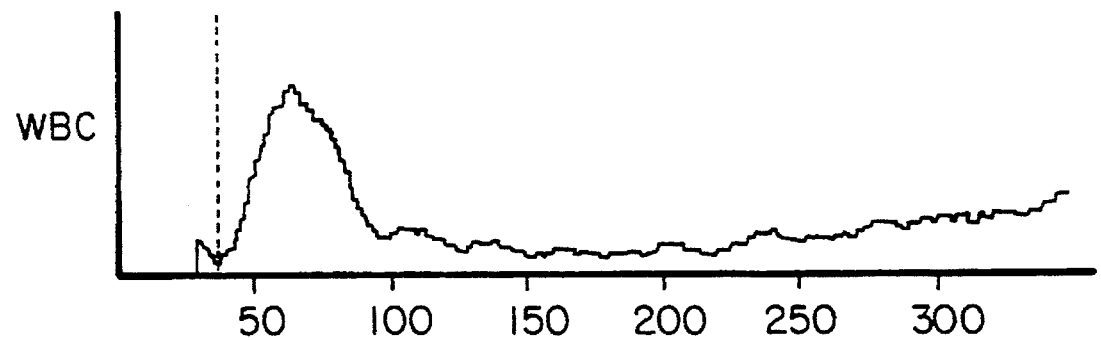
FIG. 2 is a leukocyte volume histogram showing the distribution of a patient with all normal leukocyte subpopulations obtained using the lyric reagent and blood diluent of the present invention.
Figure 3:
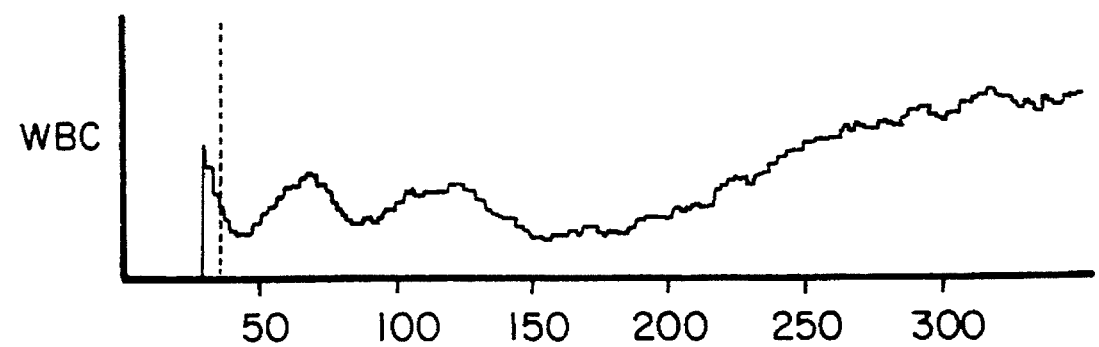
FIG. 3 is a leukocyte volume histogram showing the distribution of a patient with lymphopenia, granulocytosis and normal basophil, monocyte and eosinophil percentage using the lytic reagent and blood diluent of the present invention.

Three different human blood samples were analyzed in accordance with the foregoing. The resulting histograms are reproduced in FIGS. 1–3, respectively. As illustrated in FIGS. 1–3, the reagent system of the present invention effected a clear three component separation of white blood cell subpopulations.

The 800 cell manual differential counts have been used to establish the reference method values for the following figures in accordance with the NCCLS standard for Reference Leukocyte Differential Count And Evaluation Of Instrumental Methods. These results are recorded in Table 1.

TABLE 1

| FIGURE | Lympho-cytes | Baso-phils | Mono-cytes | Eosino-phils | Neutro-phils |
|---|---|---|---|---|---|
| 1 | 61 | 0 | 10 | 2 | 27 |
| 2 | 32 | 2 | 4 | 1 | 61 |
| 3 | 7 | 0 | 8 | 8 | 82 |

EXAMPLE 2

This example illustrates that the reagent system of the present invention including the lytic reagent composition and blood diluent, is capable of effecting an improved three component separation of white blood cells on commercially available semi-automated particle analyzers when compared to the reagent systems conventionally employed on such analyzers.

In each of the experiments herein, the semi-automated analyzer was run in accordance with the manufacturer's instructions, using either the reagent system of the present invention or the reagent system recommended by the manufacturer and routinely employed in the semi-automated analyzers. All other parameters were maintained constant. Four different whole blood samples were analyzed on a CELL-DYN® 1500 semi-automated blood analyzer available from Unipath (Mountain View, Calif.). The lyric reagent composition and blood diluent were the same as in Example 1.

Figure 4B:
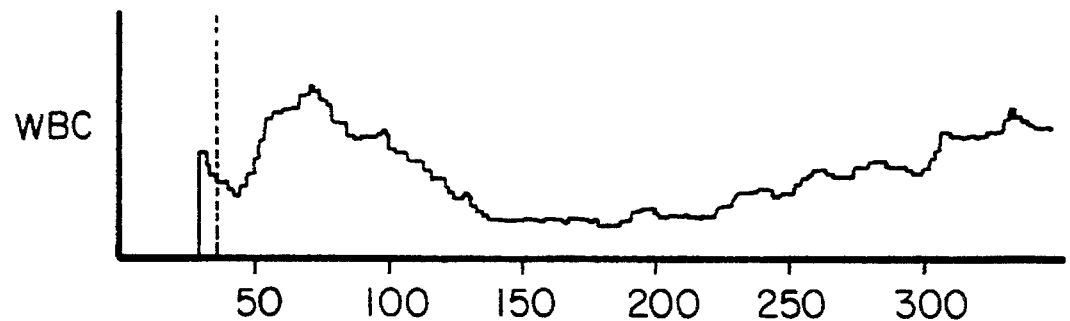
FIG. 4B is a comparative leukocyte volume histogram obtained as in FIG. 4A, but using the reagent system supplied by the manufacturers of the CELL-DYN® 1500 semi-automated analyzer.
Figure 4A:
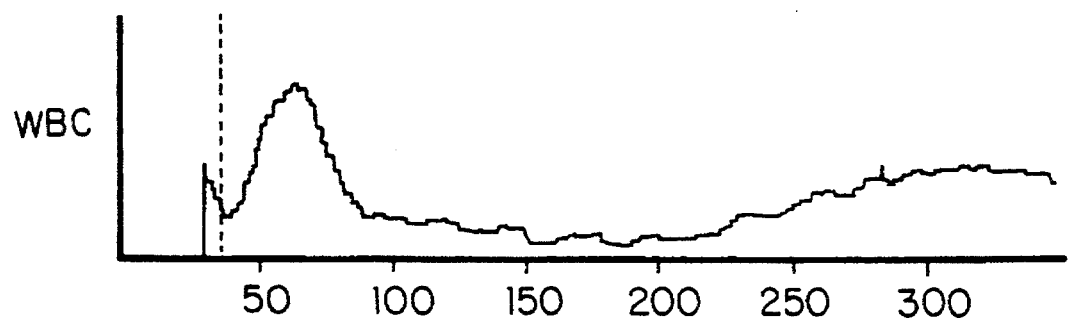
FIG. 4A is a leukocyte volume histogram prepared in accordance with the present invention using a lytic reagent composition comprising 1-dodecyl pyridinium chloride and shows the distribution of a patient with normal values for all leukocyte subpopulations. The analysis was conducted on a CELL-DYN® 1500 Semi-Automated Analyzer (Unipath, Mountain View, Calif.).
Figure 5A:
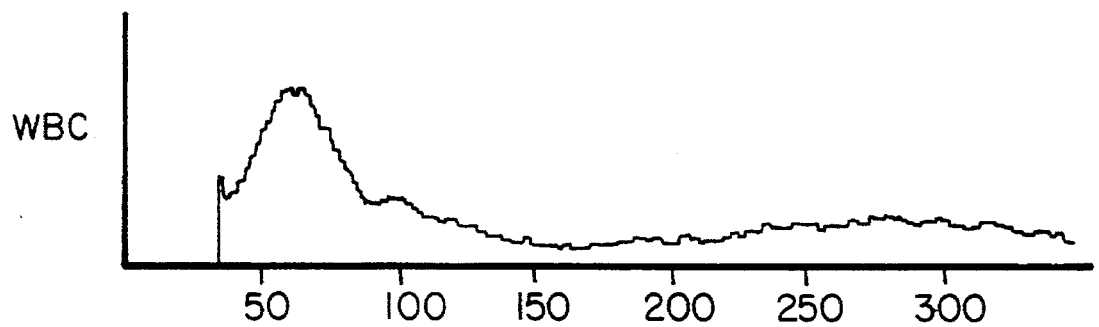
FIG. 5A is a leukocyte volume histogram prepared in accordance with the present invention using the same lytic reagent as in FIG. 4A and shows the distribution of a patient with a slightly elevated monocyte percentage, monocytosis, but all other subpopulations are normal.
Figure 5B:
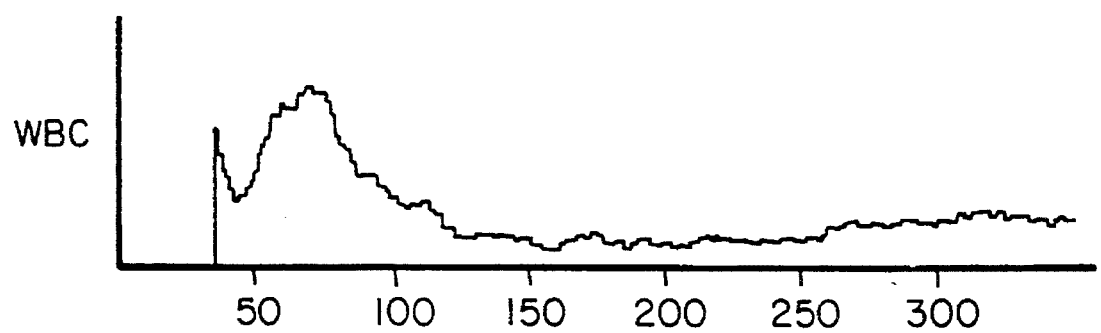
FIG. 5B is a comparative leukocyte volume histogram obtained as in FIG. 5A, but using the reagent system supplied by the manufacturer of the CELL-DYN® 1500 semi-automated analyzer.
Figure 6A:
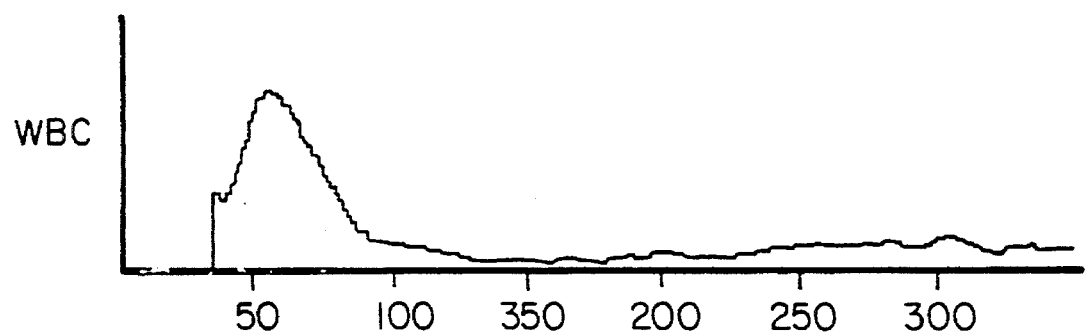
FIG. 6A is a leukocyte volume histogram prepared in accordance with the present invention using the same lytic reagent as in FIG. 4A and shows the distribution of a patient with an increased percentage of lymphocytes, normal basophil, monocyte and eosinophil percentages, and a decreased neutrophil percentage.
Figure 6B:
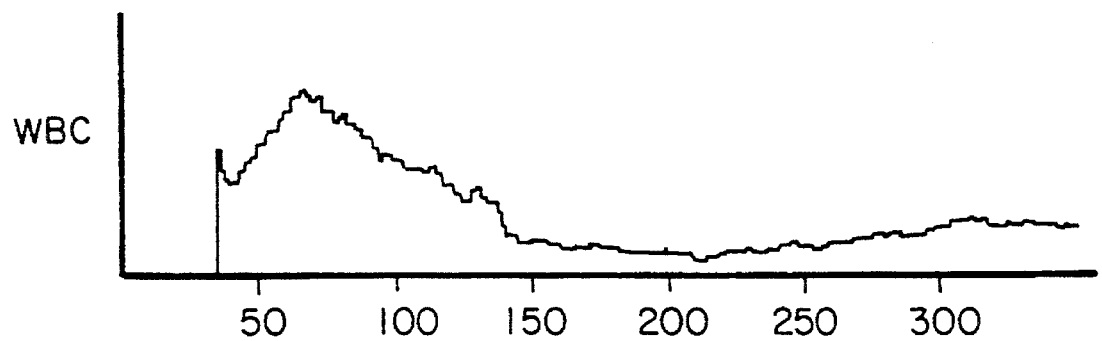
FIG. 6B is a comparative leukocyte volume histogram obtained as in FIG. 6A, but using the reagent system supplied by the manufacturer of the CELL-DYN® 1500 semi-automated analyzer.
Figure 7A:
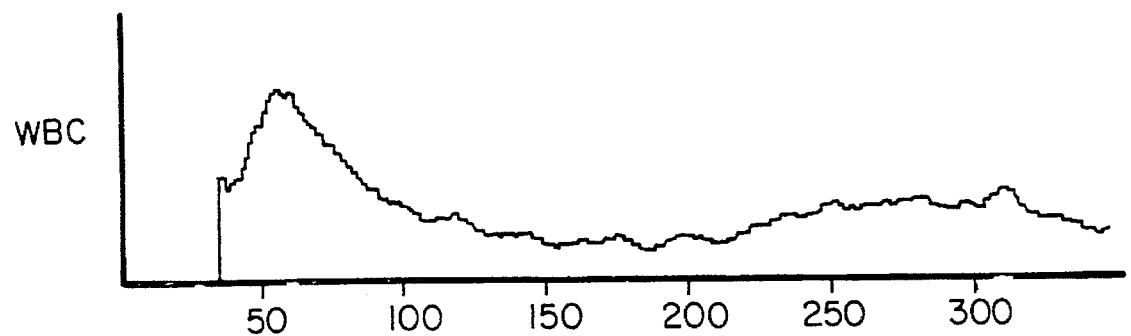
FIG. 7A is a leukocyte volume histogram prepared in accordance with the present invention using the same lytic reagent as in FIG. 4A and shows complete lysis of the erythrocytes.
Figure 7B:
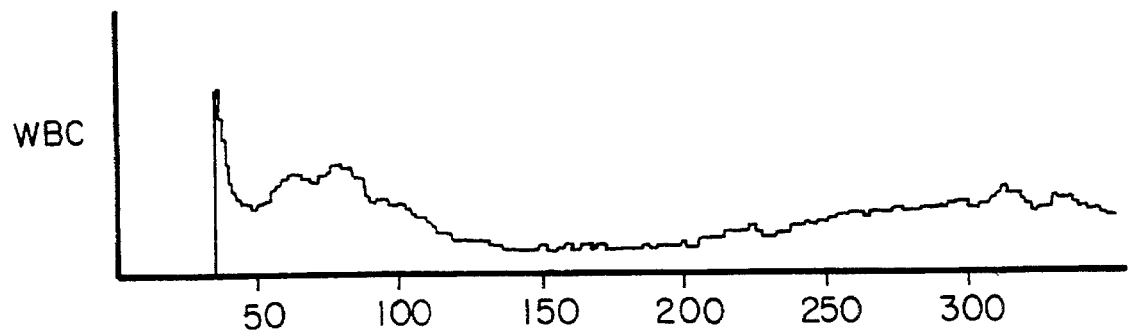
FIG. 7B is a comparative leukocyte volume histogram obtained as in FIG. 7A but using the reagent system supplied by the manufacturer of the CELL-DYN® 1500 semi-automated analyzer and shows incomplete lysis of the erythrocytes with excessive red blood cell stroma causing lower threshold interference.

The lytic reagent composition was run on the CELL-DYN® 1500 semi-automated analyzer in combination with the blood diluent and whole blood samples 4, 5, 6 and 7. The resulting histograms are set forth in FIGS. 4A, 5A, 6A and 7A, respectively. For the purpose of comparison, the same blood samples were then also run on the semi-automated instrument using the reagent system supplied by the manufacturer. The resulting comparative histograms are reproduced as FIGS. 4B, 5B, 6B and 7B, respectively. As is apparent from a comparison of FIG. 4A with FIG. 4B, FIG. 5A with FIG. 5B, FIG. 6A with FIG. 6B, and FIG. 7A with 7B, in each instance a cleaner separation was effected utilizing the reagent system, including the lytic reagent composition and blood diluent of the present invention.

The 800 cell manual differential counts have been used to establish the reference method values for the following figures in accordance with the NCCLS standard for Reference Leukocyte Differential Count And Evaluation Of Instrumental Methods. These results are recorded in Table 2.

TABLE 2

| FIGURE | Lympho-cytes | Baso-phils | Mono-cytes | Eosino-phils | Neutro-phils |
|---|---|---|---|---|---|
| 4A & 4B | 29 | 0 | 7 | 1 | 63 |
| 5A & 5B | 36 | 0 | 12 | 2 | 50 |
| 6A & 6B | 45 | 1 | 10 | 4 | 40 |
| 7A & 7B | 31 | 0 | 6 | 1 | 62 |

EXAMPLE 3

This example illustrates the preparation of a preferred lyric reagent composition of the present invention and the use of the lytic reagent composition in an automated differential analyzer to effect a three component separation of white blood cells from a sample of canine whole blood.

An example of a preferred lytic reagent composition in accordance with the invention was formulated in accordance with the following:

| Component | Amount per liter |
| --- | --- |
| 1-dodecyl pyridinium chloride | 105.0 grams |
| water | sufficient to make one liter |

This lytic reagent composition is suitable for use with diluted blood samples. In this example the blood diluent had the following formulation:

| Component | Amount per liter |
| --- | --- |
| sodium sulfate | 9.7 gm/liter |
| sodium chloride | 4.0 gm/liter |
| organic buffer | 2.0 gm/liter |
| formaldehyde | 1.0 ml/liter |
| water | sufficient for one liter |

A 280 μl sample of the lytic reagent composition was rapidly dispensed into the counting cuvette of the automated analyzer with 2.0 ml. of the blood diluent (the initial diluent) using a precise metering device, i.e., a syringe. 20 μl of whole blood sample was partitioned off using a pipetting tip and rapidly dispensed into the counting cuvette with 2.7 ml of the blood diluent (final diluent) using a syringe, to obtain a total diluent volume of 4.7 ml and a final total volume in the counting cuvette of 5.0 ml. The reagents were dispensed at a rate and in such a fashion to accomplish a rapid and thorough mixing of the sample.

Figure 8:
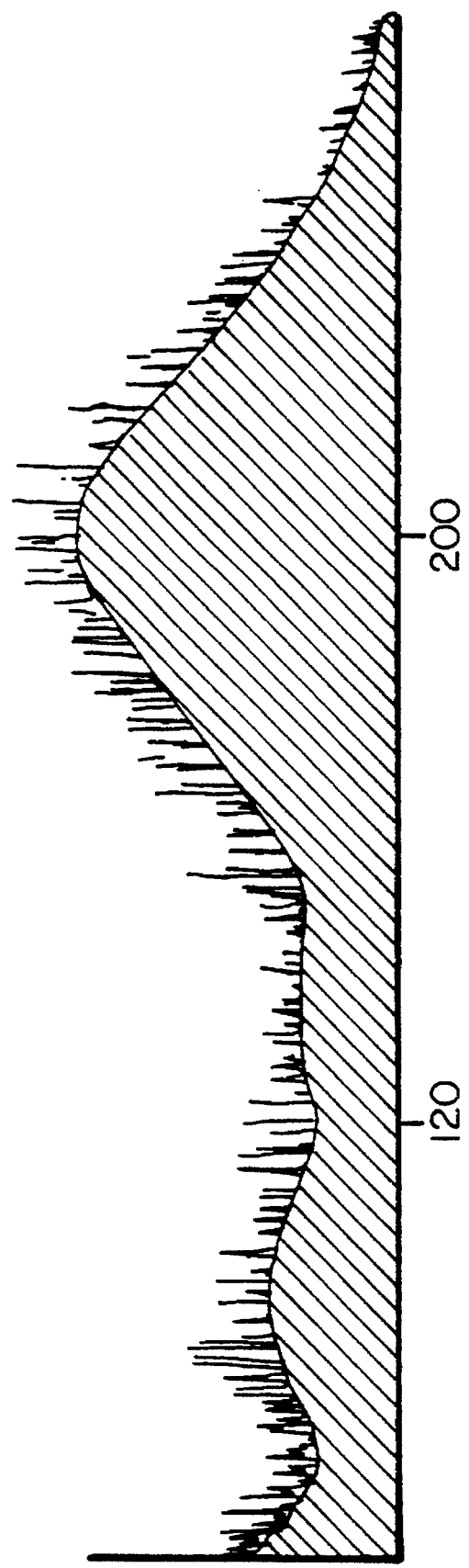
FIG. 8 is a leukocyte volumetric histogram showing the total number of cells versus cell volume for a canine specimen, which was analyzed using the methodology and reagent system of the present invention.

The diluted sample was analyzed for leukocyte volume and enumeration by electronic resistance measurements of the sample passing through an orifice. Scanning was conducted for 10 seconds after addition of the reagent system. The resulting histogram is reproduced in FIG. 8.

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A blood analysis reagent system for the automated or semi-automated differential analysis of white blood cells, comprising:

(1) an aqueous solution of an active lytic reagent consisting essentially of at least one heterocyclic quaternary ammonium compound represented by the formula:

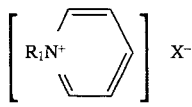

wherein $R_1$ is a long chain alkyl radical containing from 8 to 20 carbon atoms and X is a halide;
   wherein said heterocyclic quaternary ammonium compound(s) of said lytic reagent are present in a quantity sufficient to effect at least a three component differential separation of white blood cells; in combination with (2) an isotonic blood diluent comprising at least one organic buffer and a cell membrane stabilizing and antimicrobial agent, wherein said cell membrane stabilizing and antimicrobial agent comprises a monoaldehyde, said monoaldehyde being present in the range of 0.01% to 0.15% by volume of said diluent.

2. A blood analysis reagent composition according to claim 1 wherein the monoaldehyde is formaldehyde.

3. A blood analysis reagent composition according to claim 1 wherein the heterocyclic quaternary ammonium compound is at least one 1-dodecyl pyridinium halide.

4. A blood analysis reagent system according to claim 1 wherein the buffer comprises at least one member selected from the group consisting of ADA, MOPS, PIPES, HERPES, BES, BIS-TRIS, TES-TAPSO, MES, DIPSO, MOPSO, TRIS and ACES.

5. A blood analysis reagent system is defined in claim 1 additionally containing a chromogen forming reagent.

6. A blood analysis reagent system is defined in claim 5 wherein the chromagen forming reagent is potassium cyanide.

7. A reagent kit for use in the automated or semi-automated differential analysis of white blood cells comprising:

(a) a predetermined volume of a lyric reagent composition, for stromatolyzing red blood cells and selectively shrinking white blood cells into at least three subpopulations; and (b) an isotonic blood diluent, wherein the lyric reagent composition comprises:
      an aqueous solution of an active lytic reagent consisting essentially of an heterocyclic quaternary ammonium compound that is represented by the general formula

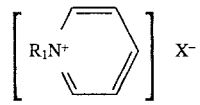

wherein $R_1$ is a long chain alkyl radical comprising from 8 to 20 carbon atoms and X is a halide;
      wherein the heterocyclic quaternary ammonium compound of said lyric reagent is present in a total concentration sufficient to effect at least a three component differential separation of white blood cells;
      and the isotonic blood diluent comprises at least one organic buffer and a cell membrane stabilizing and antimicrobial agent, wherein said cell membrane stabilizing and antimicrobial agent is a monoaldehyde, said monoaldehyde being present in the range of 0.01% to 0.15% by volume of said diluent.

8. A reagent kit according to claim 7 wherein the monoaldehyde is formaldehyde.

9. A reagent kit according to claim 7 wherein the buffer comprises at least one member selected from the group consisting of ADA, MOPS, PIPES, HEPES, BES, BIS-TRIS, TES, TAPSO, MES, DIPSO, MOPSO, TRIS and ACES.

10. A reagent kit according to claim 7, wherein the reagent composition comprises an aqueous solution of active lytic reagent comprising 1-dodecyl pyridinium chloride.

11. A reagent kit according to claim 7, wherein the lytic reagent composition further comprises a chromogen forming reagent.

12. A reagent kit according to claim 11, wherein the chromogen forming reagent is potassium cyanide.

* * * * *